United States Patent
Ebright et al.

(10) Patent No.: US 10,800,725 B2
(45) Date of Patent: Oct. 13, 2020

(54) ARYLPROPIONYL-TRIKETONE ANTIBACTERIAL AGENTS

(76) Inventors: Richard H. Ebright, New Brunswick, NJ (US); Juan Shen, New Brunswick, NJ (US)

( * ) Notice: Subject to any disclaimer, the term of this patent is extended or adjusted under 35 U.S.C. 154(b) by 1059 days.

(21) Appl. No.: 13/821,787

(22) PCT Filed: Sep. 7, 2011

(86) PCT No.: PCT/US2011/050708
§ 371 (c)(1),
(2), (4) Date: May 29, 2013

(87) PCT Pub. No.: WO2012/033846
PCT Pub. Date: Mar. 15, 2012

(65) Prior Publication Data
US 2013/0289128 A1    Oct. 31, 2013

Related U.S. Application Data

(60) Provisional application No. 61/381,117, filed on Sep. 9, 2010, provisional application No. 61/498,385, filed on Jun. 17, 2011.

(51) Int. Cl.
| C07C 49/723 | (2006.01) |
| C07C 49/747 | (2006.01) |
| C07C 49/753 | (2006.01) |

(52) U.S. Cl.
CPC .......... *C07C 49/723* (2013.01); *C07C 49/747* (2013.01); *C07C 49/753* (2013.01); *C07C 2601/16* (2017.05)

(58) Field of Classification Search
CPC ... C07C 49/723; C07C 49/747; C07C 49/753; C07C 2101/16; C07C 2601/16
See application file for complete search history.

(56) References Cited

U.S. PATENT DOCUMENTS

| 4,061,769 | A | 12/1977 | Ohno et al. |
| 4,421,763 | A | 12/1983 | Hamano et al. |
| 6,022,983 | A | 2/2000 | Wuonola et al. |
| 6,169,181 | B1 | 1/2001 | Romines et al. |
| 6,191,288 | B1 | 2/2001 | Ramamoorthy |
| 6,228,882 | B1 | 5/2001 | Wuonola et al. |
| 8,772,332 | B2 | 7/2014 | Ebright et al. |
| 2003/0065039 | A1 | 4/2003 | Kharazmi et al. |
| 2005/0187170 | A1 | 8/2005 | Bantia et al. |
| 2006/0100291 | A1 | 5/2006 | Perry et al. |
| 2007/0292355 | A1 | 12/2007 | Tamarkin et al. |
| 2013/0237595 | A1 | 9/2013 | Ebright et al. |

FOREIGN PATENT DOCUMENTS

| JP | 10324657 | * 12/1998 |
| WO | WO 98/52899 | * 11/1998 |
| WO | WO 2007/094799 | 8/2007 |
| WO | WO 2012/033846 | 3/2012 |
| WO | WO 2013/142812 | 9/2013 |
| WO | WO 2013/192352 | 12/2013 |

OTHER PUBLICATIONS

English Translation of JP-10324657.*
U.S. Appl. No. 14/370,395.
U.S. Appl. No. 13/821,804, 8,772,332.
U.S. Appl. No. 13/822,935, 2013-0237595.
PCT/US2013/033548, WO 2013/142812.
PCT/US2013/046655, WO 2013/192352.
Andre et al. "Novel synthetic molecules targeting the bacterial RNA polymerase assembly", *Journal of Antimicrobial Chemotherapy*, 57, 245-251 (2006).
Chatterjee et al., "Isolation and structure of archangelenone. Flavonoid constituent of Angelica archangelica", XP002692911, Database Caplus [Online] Chemical Abstracts accession No. 1973:489536. (1973).
Doundoulakis et al., "Myxopyronin B analogs as inhibitors of RNA polymerase, synthesis and biological evaluation", *Bioorganic & Medicinal Chemistry Letters 14*, 5667-5672 (2004).
Doundoulakis et al., "Myxopyronin B analogs as inhibitors of RNA polymerase, synthesis and biological evaluation", HCAPLUS Accession No. 2004:863124, 5 pages, Bioorganic & Medicinal Chemistry Letters, 14(22), 5667-5672 (2004).
Hu, "Total syntheses of biologically active natural products: motuporin, oleandolide, (±) -myxopyronin A and B", HCAPLUS Accession No. 2000:514322, 1 page, Diss. Abstr. Int., B 2000, 60(10), 5094. (2000).
Lira et al., "Syntheses of novel myxopyronin B analogs as potential inhibitors of bacterial RNA polymerase", *Bioorganic & Medicinal Chemistry Letters 17*, 6797-6800 (2007).
Mukhopadhyay et al., "The RNA Polymerase "Switch Region" is a Target for Inhibitors", *Cell 135*, 295-307 (2008).
Mukhopadhyay et al., "The RNA polymerase "switch region" is a target for inhbitiors" HCAPLUS Accession No. 2008:1312023, 2 pages, Cell 135(2), 295-307 (2008).
Patent Cooperation Treaty, International Searching Authority, Search Report and Written Opinion for PCT/US11/50708, 10 pages, dated Jan. 27, 2012.
Werner et al., "Synthesis of non-natural flavanones and dihydrochalcones in metabolically engineered yeast", *Journal of Molecular Catalysis B: Enzymatic 66*, 257-26 (2010).

* cited by examiner

*Primary Examiner* — Kara R McMillian
(74) *Attorney, Agent, or Firm* — Viksnins Harris Padys Malen LLP

(57) ABSTRACT

The invention provides a compound of formula (I): or a salt thereof, wherein $R^1$-$R^5$ have any of the values described in the specification, as well as compositions comprising a compound of formula (I). The compounds are useful as RNA polymerase inhibitors and antibacterial agents.

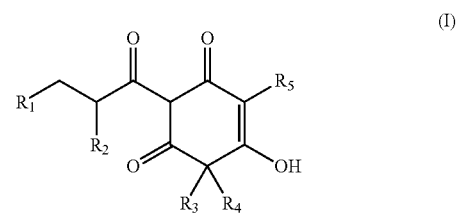

(I)

2 Claims, No Drawings

ARYLPROPIONYL-TRIKETONE ANTIBACTERIAL AGENTS

PRIORITY OF INVENTION

This application claims priority to U.S. Provisional Application Nos. 61/381,117, filed 9 Sep. 2010 and 61/498,385, filed 17 Jun. 2011.

GOVERNMENT FUNDING

The invention described herein was made with United States Government support under Grant Numbers AI072766 and AI090837 awarded by the National Institutes of Health. The United States Government has certain rights in the invention.

BACKGROUND OF THE INVENTION

The emergence of multidrug-resistant (MDR) bacterial pathogens (e.g. methicillin-resistant *Staphylococcus aureus*, MRSA) has increased concerns as to the adequacy of current antimicrobials and pathogen treatment methods. The lethality of such pathogens has often led to treatment methods that are experimental or would otherwise normally be avoided in standard clinical practice. For example, the antibiotic colistin was traditionally considered too nephrotoxic and neurotoxic for clinical use, but is nevertheless used to treat MDR bacterial infections due to a paucity of available active drugs. The growing threat from MDR pathogens highlights a critical need for new antibiotics that exhibit novel mechanisms of action and/or that are able to circumvent known resistance pathways.

SUMMARY OF THE INVENTION

Applicant has identified compounds that inhibit bacterial RNA polymerase and inhibit bacterial growth. Accordingly, in one embodiment the invention provides a compound of formula I:

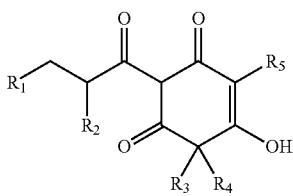

I wherein:

$R_1$ is one of aryl and heteroaryl, and optionally is substituted with one or more groups independently selected from halo, hydroxy, carboxy, cyano, nitro, trifluoromethyl, trifluoromethoxy, $(C_1-C_6)$alkyl, $(C_2-C_6)$alkenyl, $(C_1-C_6)$alkoxy, $(C_1-C_6)$alkoxycarbonyl, $(C_1-C_6)$alkanoyloxy, aryl, heteroaryl, aryloxy, heteroaryloxy, and —$NR^aR^b$;

$R_2$ is one of H, halo, hydroxy, carboxy, cyano, $(C_1-C_6)$alkyl, $(C_2-C_6)$alkenyl, $(C_2-C_6)$alkynyl, $(C_1-C_6)$alkoxy, $(C_1-C_6)$alkoxycarbonyl, $(C_1-C_6)$alkanoyloxy, aryl, heteroaryl, aryloxy, heteroaryloxy, or —$NR^cR^d$, wherein any $(C_1-C_6)$alkyl, $(C_2-C_6)$alkenyl, $(C_2-C_6)$alkynyl, $(C_1-C_6)$alkoxy, $(C_1-C_6)$alkoxycarbonyl, $(C_1-C_6)$alkanoyloxy, aryl, and heteroaryl, and is optionally substituted with one or more halo, hydroxy, carboxy, cyano, nitro, $(C_1-C_6)$alkoxy, $(C_1-C_6)$alkoxycarbonyl, $(C_1-C_6)$alkanoyloxy or —$NR^cR^d$;

$R_3$ is $(C_1-C_7)$alkyl or $(C_2-C_7)$alkenyl, which $(C_1-C_7)$alkyl or $(C_2-C_7)$alkenyl is optionally substituted with one or more groups independently selected from oxo, halo, hydroxy, carboxy, cyano, nitro, trifluoromethyl, trifluoromethoxy, $(C_1-C_6)$alkyl, $(C_1-C_6)$alkoxy, $(C_1-C_6)$alkoxycarbonyl, $(C_1-C_6)$alkanoyloxy, aryl, heteroaryl, aryloxy, heteroaryloxy, and —$NR^eR^f$;

$R_4$ is H, $(C_1-C_7)$alkyl or $(C_2-C_7)$alkenyl, which $(C_1-C_7)$alkyl or $(C_2-C_7)$alkenyl is optionally substituted with one or more groups independently selected from oxo, halo, hydroxy, carboxy, cyano, nitro, trifluoromethyl, trifluoromethoxy, $(C_1-C_6)$alkyl, $(C_1-C_6)$alkoxy, $(C_1-C_6)$alkoxycarbonyl, $(C_1-C_6)$alkanoyloxy, aryl, heteroaryl, aryloxy, heteroaryloxy, and —$NR^gR^h$;

$R_5$ is H, $(C_1-C_7)$alkyl or $(C_2-C_7)$alkenyl, which $(C_1-C_7)$alkyl or $(C_2-C_7)$alkenyl is optionally substituted with one or more groups independently selected from oxo, halo, hydroxy, carboxy, cyano, nitro, trifluoromethyl, trifluoromethoxy, $(C_1-C_6)$alkyl, $(C_1-C_6)$alkoxy, $(C_1-C_6)$alkoxycarbonyl, $(C_1-C_6)$alkanoyloxy, aryl, heteroaryl, aryloxy, heteroaryloxy, and —$NR^jR^k$;

$R^a$ and $R^b$ are each independently H, $(C_1-C_6)$alkyl, aryl, heteroaryl, aryl$(C_1-C_6)$alkyl or heteroaryl$(C_1-C_6)$alkyl; or $R^a$ and $R^b$ together with the nitrogen to which they are attached form a morpholino, piperazino, pyrrolidino or piperidino;

$R^c$ and $R^d$ are each independently H, $(C_1-C_6)$alkyl, aryl, heteroaryl, aryl$(C_1-C_6)$alkyl, or heteroaryl$(C_1-C_6)$alkyl; or $R^c$ and $R^d$ together with the nitrogen to which they are attached form a morpholino, piperazino, pyrrolidino or piperidino;

$R^e$ and $R^f$ are each independently H, $(C_1-C_6)$alkyl, aryl, heteroaryl, aryl$(C_1-C_6)$alkyl, or heteroaryl$(C_1-C_6)$alkyl; or $R^e$ and $R^f$ together with the nitrogen to which they are attached form a morpholino, piperazino, pyrrolidino or piperidino;

$R^g$ and $R^h$ are each independently H, $(C_1-C_6)$alkyl, aryl, heteroaryl, aryl$(C_1-C_6)$alkyl, or heteroaryl$(C_1-C_6)$alkyl; or $R^g$ and $R^h$ together with the nitrogen to which they are attached form a morpholino, piperazino, pyrrolidino or piperidino; and $R^j$ and $R^k$ are each independently H, $(C_1-C_6)$alkyl, aryl, heteroaryl, aryl$(C_1-C_6)$alkyl, or heteroaryl$(C_1-C_6)$alkyl; or $R^j$ and $R^k$ together with the nitrogen to which they are attached form a morpholino, piperazino, pyrrolidino or piperidino; or a salt thereof.

The invention also provides a composition comprising a compound of formula I or a pharmaceutically acceptable salt thereof and a pharmaceutically acceptable vehicle.

The invention also provides a method for inhibiting a bacterial RNA polymerase comprising contacting the bacterial RNA polymerase with a compound of formula I or a salt thereof.

The invention also provides a method for inhibiting the growth of a bacterium comprising contacting the bacterium with a compound of formula I or a salt thereof.

The invention also provides a method for treating a bacterial infection in a mammal comprising administering to the mammal an effective amount of a compound of formula I or a pharmaceutically acceptable salt thereof.

The invention also provides a compound of formula I or a pharmaceutically acceptable salt thereof for use in the prophylactic or therapeutic treatment of a bacterial infection.

The invention also provides a compound of formula I or a pharmaceutically acceptable salt thereof for use in medical treatment.

The invention also provides the use of a compound of formula I or a pharmaceutically acceptable salt thereof for the preparation of a medicament for treating a bacterial infection in a mammal.

The invention also provides the use of a compound of formula I or a salt thereof as a disinfectant, sterilant, antispoilant, or antiseptic.

The invention also provides synthetic processes and intermediates disclosed herein that are useful for preparing compounds of formula (I) or salts thereof.

DETAILED DESCRIPTION

The following definitions are used, unless otherwise described: halo is fluoro, chloro, bromo, or iodo. Alkyl, alkoxy, alkenyl, alkynyl, etc. denote both straight and branched groups; but reference to an individual radical such as propyl embraces only the straight chain radical, a branched chain isomer such as isopropyl being specifically referred to. Aryl denotes a phenyl radical or an ortho-fused bicyclic carbocyclic radical having about nine to ten ring atoms in which at least one ring is aromatic. Heteroaryl encompasses a radical of a monocyclic aromatic ring containing five or six ring atoms consisting of carbon and one to four heteroatoms each selected from the group consisting of non-peroxide oxygen, sulfur, and N(X) wherein X is absent or is H, O, $(C_1-C_4)$alkyl, phenyl or benzyl, as well as a radical of an ortho-fused bicyclic heterocycle of about eight to ten ring atoms comprising one to four heteroatoms each selected from the group consisting of non-peroxide oxygen, sulfur, and N(X).

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

It will also be appreciated that compounds of the invention can exist in different tautomeric forms. The compounds of formula I also encompasses any tautomeric forms or mixtures thereof. For example, two possible tautomeric forms of a compound of formula I are illustrated below in Scheme 1.

Scheme 1

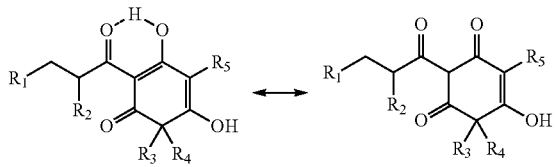

Specific values listed below for radicals, substituents, and ranges, are for illustration only; they do not exclude other defined values or other values within defined ranges for the radicals and substituents Specifically, $(C_1-C_6)$alkyl can be methyl, ethyl, propyl, isopropyl, butyl, iso-butyl, sec-butyl, pentyl, 3-pentyl, or hexyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_2-C_6)$alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; $(C_2-C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_1-C_6)$alkanoyl can be acetyl, propanoyl or butanoyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_1-C_6)$alkanoyloxy can be formyloxy, acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazoyl, isoxazoyl, thiazolyl, isothiazolyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

In one specific embodiment the invention provides a compound of formula I wherein:

$R_1$ is one of aryl and heteroaryl, and optionally is substituted with one or more groups independently selected from halo, hydroxy, carboxy, cyano, nitro, trifluoromethyl, trifluoromethoxy, $(C_1-C_6)$alkyl, $(C_1-C_6)$alkoxy, $(C_1-C_6)$alkoxycarbonyl, $(C_1-C_6)$alkanoyloxy, aryl, heteroaryl, aryloxy, heteroaryloxy, and $-NR^aR^b$;

$R_2$ is H or methyl;

$R_3$ is $(C_3-C_6)$alkyl, which is optionally substituted with one or more groups independently selected from oxo, halo, hydroxy, carboxy, cyano, nitro, trifluoromethyl, trifluoromethoxy, $(C_1-C_6)$alkyl, $(C_1-C_6)$alkoxy, $(C_1-C_6)$alkoxycarbonyl, $(C_1-C_6)$alkanoyloxy, aryl, heteroaryl, aryloxy, heteroaryloxy, and $-NR^eR^f$;

$R_4$ is $(C_3-C_6)$alkyl, which is optionally substituted with one or more groups independently selected from oxo, halo, hydroxy, carboxy, cyano, nitro, trifluoromethyl, trifluoromethoxy, $(C_1-C_6)$alkyl, $(C_1-C_6)$alkoxy, $(C_1-C_6)$alkoxycarbonyl, $(C_1-C_6)$alkanoyloxy, aryl, heteroaryl, aryloxy, heteroaryloxy, and $-NR^gR^h$;

$R_5$ is H or $(C_3-C_6)$alkyl, which is optionally substituted with one or more groups independently selected from oxo, halo, hydroxy, carboxy, cyano, nitro, trifluoromethyl, trifluoromethoxy, $(C_1-C_6)$alkyl, $(C_1-C_6)$alkoxy, $(C_1-C_6)$alkoxycarbonyl, $(C_1-C_6)$alkanoyloxy, aryl, heteroaryl, aryloxy, heteroaryloxy, and $-NR^jR^k$;

$R^a$ and $R^b$ are each independently H, $(C_1-C_6)$alkyl, aryl, heteroaryl, aryl$(C_1-C_6)$alkyl, or heteroaryl$(C_1-C_6)$alkyl; or $R^a$ and $R^b$ together with the nitrogen to which they are attached form a morpholino, piperazino, pyrrolidino or piperidino;

$R^e$ and $R^f$ are each independently H, $(C_1-C_6)$alkyl, aryl, heteroaryl, aryl$(C_1-C_6)$alkyl, or heteroaryl$(C_1-C_6)$alkyl; or $R^e$ and $R^f$ together with the nitrogen to which they are attached form a morpholino, piperazino, pyrrolidino or piperidino; and $R^g$ and $R^h$ are each independently H, $(C_1-C_6)$alkyl, aryl, heteroaryl, aryl$(C_1-C_6)$alkyl, or heteroaryl$(C_1-C_6)$alkyl; or $R^g$ and $R^h$ together with the nitrogen to which they are attached form a morpholino, piperazino, pyrrolidino or piperidino; and $R^j$ and $R^k$ are each independently H, $(C_1-C_6)$alkyl, aryl, heteroaryl, aryl$(C_1-C_6)$alkyl, or heteroaryl$(C_1-C_6)$alkyl; or $R^j$ and $R^k$ together with the nitrogen to which they are attached form a morpholino, piperazino, pyrrolidino or piperidino;
or a salt thereof.
In one specific embodiment the invention provides the compound:
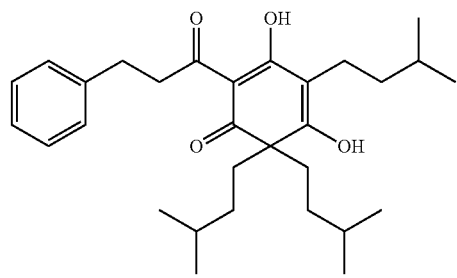
15
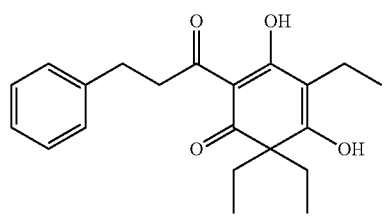
16
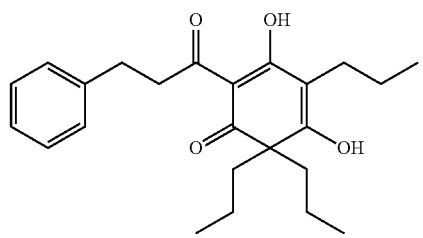
17
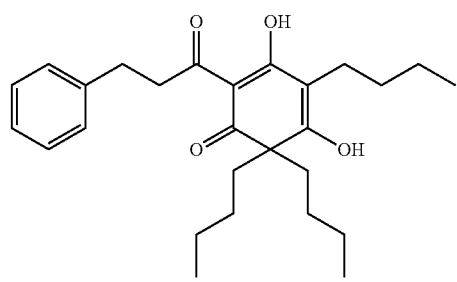
18
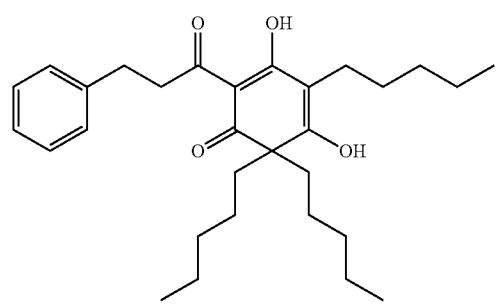
19
or
-continued
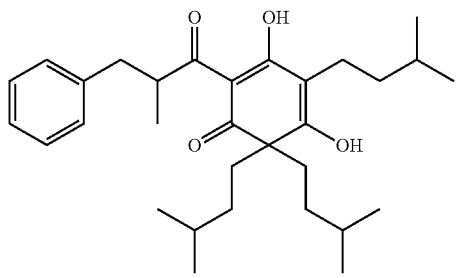
20
or a salt thereof.
In one specific embodiment the invention provides the compound:
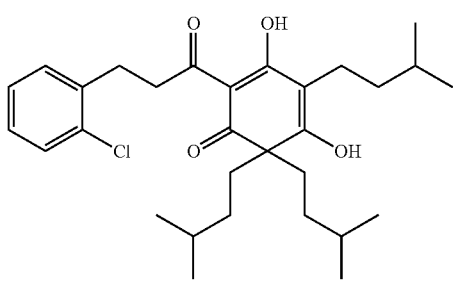 [SMILES: CC(C)CCC1=C(O)C(CCC(C)C)(CCC(C)C)C(=O)C(C(=O)CCc2ccccc2Cl)=C1O]
1
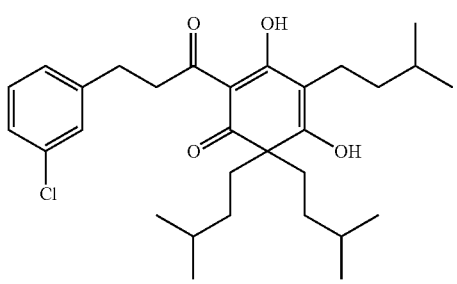 [SMILES: CC(C)CCC1=C(O)C(CCC(C)C)(CCC(C)C)C(=O)C(C(=O)CCc2cccc(Cl)c2)=C1O]
2
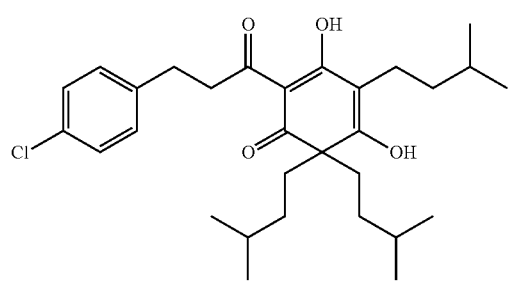 [SMILES: CC(C)CCC1=C(O)C(CCC(C)C)(CCC(C)C)C(=O)C(C(=O)CCc2ccc(Cl)cc2)=C1O]
3
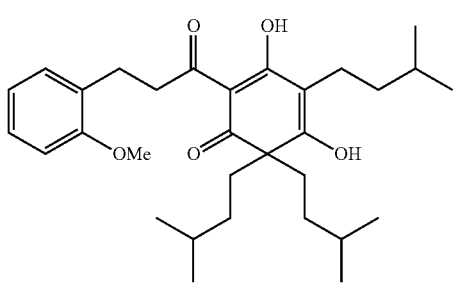 [SMILES: COc1ccccc1CCC(=O)C1=C(O)C(CCC(C)C)=C(O)C(CCC(C)C)(CCC(C)C)C1=O]
4

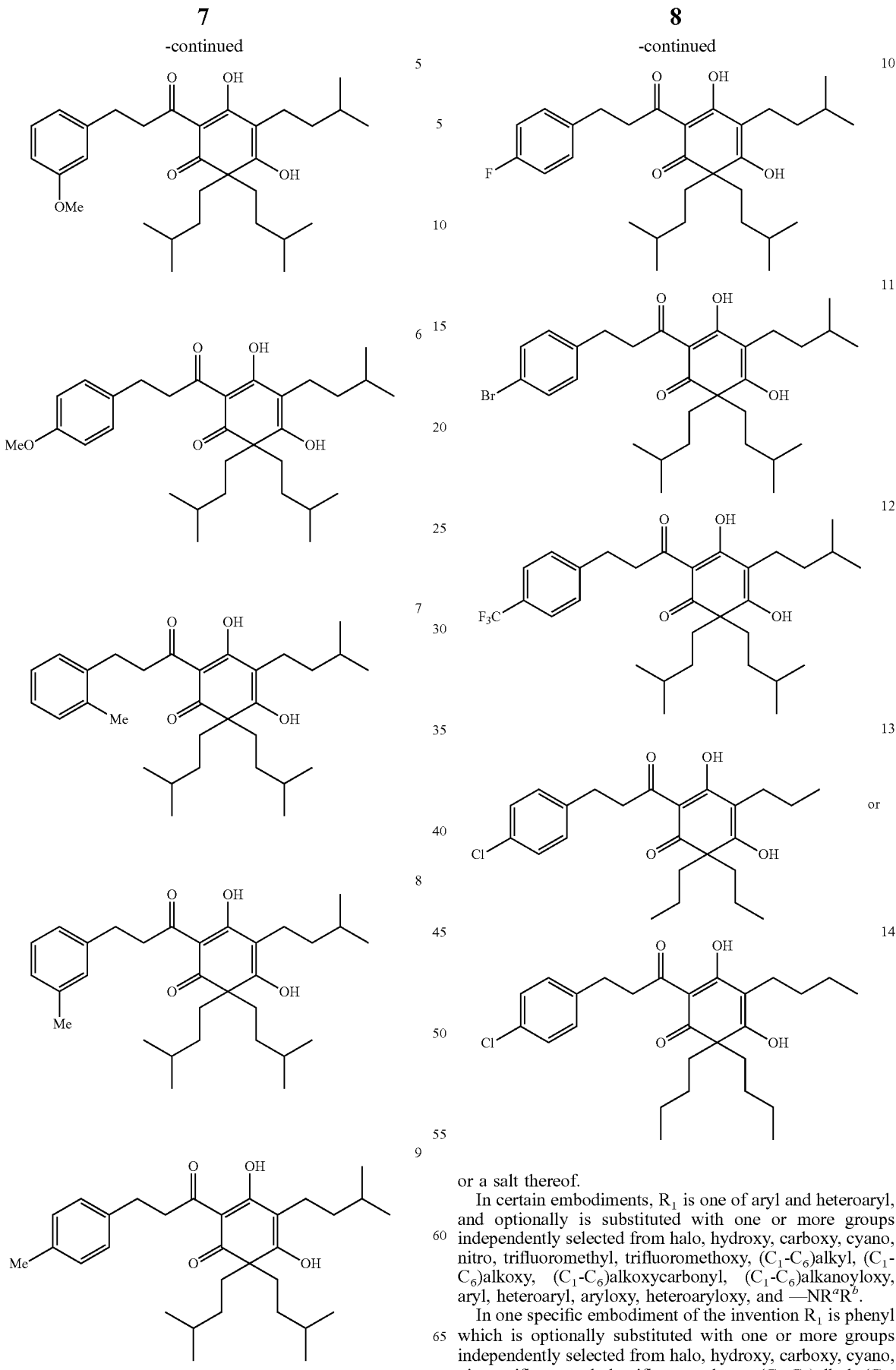

or a salt thereof.

In certain embodiments, R₁ is one of aryl and heteroaryl, and optionally is substituted with one or more groups independently selected from halo, hydroxy, carboxy, cyano, nitro, trifluoromethyl, trifluoromethoxy, $(C_1-C_6)$alkyl, $(C_1-C_6)$alkoxy, $(C_1-C_6)$alkoxycarbonyl, $(C_1-C_6)$alkanoyloxy, aryl, heteroaryl, aryloxy, heteroaryloxy, and $-NR^aR^b$.

In one specific embodiment of the invention R₁ is phenyl which is optionally substituted with one or more groups independently selected from halo, hydroxy, carboxy, cyano, nitro, trifluoromethyl, trifluoromethoxy, $(C_1-C_6)$alkyl, $(C_1$-

$C_6$)alkoxy, $(C_1-C_6)$alkoxycarbonyl, $(C_1-C_6)$alkanoyloxy, aryl, heteroaryl, aryloxy, heteroaryloxy, and —NR$^a$R$^b$.

In certain embodiments, $R_1$ is phenyl substituted at the ortho, meta, or para position with halo, $(C_1-C_6)$alkoxy, $(C_1-C_6)$alkyl or $(C_1-C_6)$alkenyl.

In certain embodiments, $R_2$ is H or methyl.

In certain embodiments, $R_3$ and $R_4$ are each independently one of $(C_1-C_7)$alkyl, $(C_1-C_7)$alkenyl, substituted $(C_1-C_7)$alkyl or substituted $(C_1-C_7)$alkenyl.

In certain embodiments, $R_5$ is one of H, $(C_1-C_7)$alkyl, $(C_1-C_7)$alkenyl, substituted $(C_1-C_7)$alkyl or substituted $(C_1-C_7)$alkenyl.

In certain embodiments, $R_3$ is $(C_3-C_6)$alkyl, which is optionally substituted with one or more groups independently selected from oxo, halo, hydroxy, carboxy, cyano, nitro, trifluoromethyl, trifluoromethoxy, $(C_1-C_6)$alkyl, $(C_1-C_6)$alkoxy, $(C_1-C_6)$alkoxycarbonyl, $(C_1-C_6)$alkanoyloxy, aryl, heteroaryl, aryloxy, heteroaryloxy, and —NR$^e$R$^f$.

In certain embodiments, $R_4$ is $(C_3-C_6)$alkyl, which is optionally substituted with one or more groups independently selected from oxo, halo, hydroxy, carboxy, cyano, nitro, trifluoromethyl, trifluoromethoxy, $(C_1-C_6)$alkyl, $(C_1-C_6)$alkoxy, $(C_1-C_6)$alkoxycarbonyl, $(C_1-C_6)$alkanoyloxy, aryl, heteroaryl, aryloxy, heteroaryloxy, and —NR$^g$R$^h$.

In certain embodiments, $R_5$ is H or $(C_3-C_6)$alkyl, which is optionally substituted with one or more groups independently selected from oxo, halo, hydroxy, carboxy, cyano, nitro, trifluoromethyl, trifluoromethoxy, $(C_1-C_6)$alkyl, $(C_1-C_6)$alkoxy, $(C_1-C_6)$alkoxycarbonyl, $(C_1-C_6)$alkanoyloxy, aryl, heteroaryl, aryloxy, heteroaryloxy, and —NR$^j$R$^k$.

In certain embodiments, $R_1$ is substituted with halo.

In certain embodiments, $R_1$ is substituted with fluorine, chlorine, or bromine.

In certain embodiments, $R_1$ is substituted with chlorine.

In certain embodiments, $R_1$ is phenyl, which is optionally substituted with one or more groups independently selected from halo, hydroxy, carboxy, cyano, nitro, trifluoromethyl, trifluoromethoxy, $(C_1-C_6)$alkyl, $(C_1-C_6)$alkoxy, $(C_1-C_6)$alkoxycarbonyl, $(C_1-C_6)$alkanoyloxy, aryl, heteroaryl, aryloxy, heteroaryloxy, and —NR$^a$R$^b$.

In certain embodiments, $R_1$ is phenyl.

In certain embodiments, $R_3$ is propyl, butyl, pentyl, or isopentyl.

In certain embodiments, $R_4$ is propyl, butyl, pentyl, or isopentyl.

In certain embodiments, $R_5$ is H.

In certain embodiments, $R_5$ is propyl, butyl, pentyl, or isopentyl.

In certain embodiments, $R_1$ is one of aryl and heteroaryl, and optionally is substituted with one or more groups independently selected from halo, hydroxy, carboxy, cyano, nitro, trifluoromethyl, trifluoromethoxy, $(C_1-C_6)$alkyl, $(C_1-C_6)$alkoxy, $(C_1-C_6)$alkoxycarbonyl, $(C_1-C_6)$alkanoyloxy, aryl, heteroaryl, aryloxy, heteroaryloxy, and —NR$^a$R$^b$; $R_2$ is one of H, halo, hydroxy, carboxy, cyano, $(C_1-C_6)$alkyl, $(C_2-C_6)$alkenyl, $(C_2-C_6)$alkynyl, $(C_1-C_6)$alkoxy, $(C_1-C_6)$alkoxycarbonyl, $(C_1-C_6)$alkanoyloxy, aryl, heteroaryl, aryloxy, heteroaryloxy, or —NR$^c$R$^d$, wherein any $(C_1-C_6)$alkyl, $(C_2-C_6)$alkenyl, $(C_2-C_6)$alkylnyl, $(C_1-C_6)$alkoxy, $(C_1-C_6)$alkoxycarbonyl, $(C_1-C_6)$alkanoyloxy, aryl, and heteroaryl, and is optionally substituted with one or more halo, hydroxy, carboxy, cyano, nitro, $(C_1-C_6)$alkoxy, $(C_1-C_6)$alkoxycarbonyl, $(C_1-C_6)$alkanoyloxy or —NR$^c$R$^d$; $R_3$ is $(C_3-C_6)$alkyl, which is optionally substituted with one or more groups independently selected from oxo, halo, hydroxy, carboxy, cyano, nitro, trifluoromethyl, trifluoromethoxy, $(C_1-C_6)$alkyl, $(C_1-C_6)$alkoxy, $(C_1-C_6)$alkoxycarbonyl, $(C_1-C_6)$al-kanoyloxy, aryl, heteroaryl, aryloxy, heteroaryloxy, and —NR$^e$R$^f$; $R_4$ is $(C_3-C_6)$alkyl, which is optionally substituted with one or more groups independently selected from oxo, halo, hydroxy, carboxy, cyano, nitro, trifluoromethyl, trifluoromethoxy, $(C_1-C_6)$alkyl, $(C_1-C_6)$alkoxy, $(C_1-C_6)$alkoxycarbonyl, $(C_1-C_6)$alkanoyloxy, aryl, heteroaryl, aryloxy, heteroaryloxy, and —NR$^g$R$^h$; $R_5$ is H or $(C_3-C_6)$alkyl, which is optionally substituted with one or more groups independently selected from oxo, halo, hydroxy, carboxy, cyano, nitro, trifluoromethyl, trifluoromethoxy, $(C_1-C_6)$alkyl, $(C_1-C_6)$alkoxy, $(C_1-C_6)$alkoxycarbonyl, $(C_1-C_6)$alkanoyloxy, aryl, heteroaryl, aryloxy, heteroaryloxy, and —NR$^j$R$^k$; $R^a$ and $R^b$ are each independently H, $(C_1-C_6)$alkyl, aryl, heteroaryl, aryl$(C_1-C_6)$alkyl or heteroaryl$(C_1-C_6)$alkyl; or $R^a$ and $R^b$ together with the nitrogen to which they are attached form a morpholino, piperazino, pyrrolidino or piperidino; $R^e$ and $R^d$ are each independently H, $(C_1-C_6)$alkyl, aryl, heteroaryl, aryl$(C_1-C_6)$alkyl, or heteroaryl$(C_1-C_6)$alkyl; or $R^c$ and $R^d$ together with the nitrogen to which they are attached form a morpholino, piperazino, pyrrolidino or piperidino;

$R^e$ and $R^f$ are each independently H, $(C_1-C_6)$alkyl, aryl, heteroaryl, aryl$(C_1-C_6)$alkyl, or heteroaryl$(C_1-C_6)$alkyl; or $R^e$ and $R^f$ together with the nitrogen to which they are attached form a morpholino, piperazino, pyrrolidino or piperidino; $R^g$ and $R^h$ are each independently H, $(C_1-C_6)$alkyl, aryl, heteroaryl, aryl$(C_1-C_6)$alkyl, or heteroaryl$(C_1-C_6)$alkyl; or $R^g$ and $R^h$ together with the nitrogen to which they are attached form a morpholino, piperazino, pyrrolidino or piperidino; and $R^j$ and $R^k$ are each independently H, $(C_1-C_6)$alkyl, aryl, heteroaryl, aryl$(C_1-C_6)$alkyl, or heteroaryl$(C_1-C_6)$alkyl; or $R^g$ and $R^h$ together with the nitrogen to which they are attached form a morpholino, piperazino, pyrrolidino or piperidino.

In one embodiment the invention provides a compound of formula I wherein:

$R_1$ is one of aryl and heteroaryl, and optionally is substituted with one or more groups independently selected from halo, hydroxy, carboxy, cyano, nitro, trifluoromethyl, trifluoromethoxy, $(C_1-C_6)$alkyl, $(C_1-C_6)$alkenyl, $(C_1-C_6)$alkoxy, $(C_1-C_6)$alkoxycarbonyl, $(C_1-C_6)$alkanoyloxy, aryl, heteroaryl, aryloxy, heteroaryloxy, and —NR$^a$R$^b$;

$R_2$ is one of H, halo, hydroxy, carboxy, cyano, $(C_1-C_6)$alkyl, $(C_2-C_6)$alkenyl, $(C_2-C_6)$alkynyl, $(C_1-C_6)$alkoxy, $(C_1-C_6)$alkoxycarbonyl, $(C_1-C_6)$alkanoyloxy, aryl, heteroaryl, aryloxy, heteroaryloxy, or —NR$^c$R$^d$, wherein any $(C_1-C_6)$alkyl, $(C_2-C_6)$alkenyl, $(C_2-C_6)$alkynyl, $(C_1-C_6)$alkoxy, $(C_1-C_6)$alkoxycarbonyl, $(C_1-C_6)$alkanoyloxy, aryl, and heteroaryl, and is optionally substituted with one or more halo, hydroxy, carboxy, cyano, nitro, $(C_1-C_6)$alkoxy, $(C_1-C_6)$alkoxycarbonyl, $(C_1-C_6)$alkanoyloxy or —NR$^c$R$^d$;

$R_3$ is $(C_1-C_7)$alkyl or $(C_1-C_7)$alkenyl, which is optionally substituted with one or more groups independently selected from oxo, halo, hydroxy, carboxy, cyano, nitro, trifluoromethyl, trifluoromethoxy, $(C_1-C_6)$alkyl, $(C_1-C_6)$alkoxy, $(C_1-C_6)$alkoxycarbonyl, $(C_1-C_6)$alkanoyloxy, aryl, heteroaryl, aryloxy, heteroaryloxy, and —NR$^e$R$^f$;

$R_4$ is $(C_1-C_7)$alkyl or $(C_1-C_7)$alkenyl, which is optionally substituted with one or more groups independently selected from oxo, halo, hydroxy, carboxy, cyano, nitro, trifluoromethyl, trifluoromethoxy, $(C_1-C_6)$alkyl, $(C_1-C_6)$alkoxy, $(C_1-C_6)$alkoxycarbonyl, $(C_1-C_6)$alkanoyloxy, aryl, heteroaryl, aryloxy, heteroaryloxy, and —NR$^g$R$^h$;

$R_5$ is H, $(C_1-C_7)$alkyl or $(C_1-C_7)$alkenyl, which $(C_1-C_7)$alkyl or $(C_1-C_7)$alkenyl is optionally substituted with one or more groups independently selected from oxo, halo, hydroxy, carboxy, cyano, nitro, trifluoromethyl, trifluoromethoxy, $(C_1-C_6)$alkyl, $(C_1-C_6)$alkoxy, $C_6)$alkoxycarbonyl, $(C_1-C_6)$alkanoyloxy, aryl, heteroaryl, aryloxy, heteroaryloxy, and $-NR^jR^k$;

$R^a$ and $R^b$ are each independently H, $(C_1-C_6)$alkyl, aryl, heteroaryl, aryl$(C_1-C_6)$alkyl or heteroaryl$(C_1-C_6)$alkyl; or $R^a$ and $R^b$ together with the nitrogen to which they are attached form a morpholino, piperazino, pyrrolidino or piperidino;

$R^c$ and $R^d$ are each independently H, $(C_1-C_6)$alkyl, aryl, heteroaryl, aryl$(C_1-C_6)$alkyl, or heteroaryl$(C_1-C_6)$alkyl; or $R^c$ and $R^d$ together with the nitrogen to which they are attached form a morpholino, piperazino, pyrrolidino or piperidino;

$R^e$ and $R^f$ are each independently H, $(C_1-C_6)$alkyl, aryl, heteroaryl, aryl$(C_1-C_6)$alkyl, or heteroaryl$(C_1-C_6)$alkyl; or $R^e$ and $R^f$ together with the nitrogen to which they are attached form a morpholino, piperazino, pyrrolidino or piperidino;

$R^g$ and $R^h$ are each independently H, $(C_1-C_6)$alkyl, aryl, heteroaryl, aryl$(C_1-C_6)$alkyl, or heteroaryl$(C_1-C_6)$alkyl; or $R^g$ and $R^h$ together with the nitrogen to which they are attached form a morpholino, piperazino, pyrrolidino or piperidino; and $R^j$ and $R^k$ are each independently H, $(C_1-C_6)$alkyl, aryl, heteroaryl, aryl$(C_1-C_6)$alkyl, or heteroaryl$(C_1-C_6)$alkyl; or $R^j$ and $R^k$ together with the nitrogen to which they are attached form a morpholino, piperazino, pyrrolidino or piperidino;

or a salt thereof.

In one embodiment the invention provides a compound of formula I wherein: $R_3$ is $(C_1-C_7)$alkyl or $(C_2-C_7)$alkenyl, which $(C_1-C_7)$alkyl or $(C_2-C_7)$alkenyl is optionally substituted with one or more groups independently selected from oxo, halo, hydroxy, carboxy, cyano, nitro, trifluoromethyl, trifluoromethoxy, $(C_1-C_6)$alkyl, $(C_1-C_6)$alkoxy, $(C_1-C_6)$alkoxycarbonyl, $(C_1-C_6)$alkanoyloxy, aryl, heteroaryl, aryloxy, heteroaryloxy, and $-NR^eR^f$; $R_4$ is $(C_1-C_7)$alkyl or $(C_2-C_7)$alkenyl, which $(C_1-C_7)$alkyl or $(C_2-C_7)$alkenyl is optionally substituted with one or more groups independently selected from oxo, halo, hydroxy, carboxy, cyano, nitro, trifluoromethyl, trifluoromethoxy, $(C_1-C_6)$alkyl, $(C_1-C_6)$alkoxy, $(C_1-C_6)$alkoxycarbonyl, $(C_1-C_6)$alkanoyloxy, aryl, heteroaryl, aryloxy, heteroaryloxy, and $-NR^gR^h$; and $R_5$ is H, $(C_1-C_7)$alkyl or $(C_2-C_7)$alkenyl, which $(C_1-C_7)$alkyl or $(C_2-C_7)$alkenyl is optionally substituted with one or more groups independently selected from oxo, halo, hydroxy, carboxy, cyano, nitro, trifluoromethyl, trifluoromethoxy, $(C_1-C_6)$alkyl, $(C_1-C_6)$alkoxy, $(C_1-C_6)$alkoxycarbonyl, $(C_1-C_6)$alkanoyloxy, aryl, heteroaryl, aryloxy, heteroaryloxy, and $-NR^jR^k$.

In one embodiment the invention provides a compound of formula I wherein: $R_3$ is $(C_3-C_7)$alkyl or $(C_3-C_7)$alkenyl, which $(C_3-C_7)$alkyl or $(C_3-C_7)$alkenyl is optionally substituted with one or more groups independently selected from oxo, halo, hydroxy, carboxy, cyano, nitro, trifluoromethyl, trifluoromethoxy, $(C_1-C_6)$alkyl, $(C_1-C_6)$alkoxy, $(C_1-C_6)$alkoxycarbonyl, $(C_1-C_6)$alkanoyloxy, aryl, heteroaryl, aryloxy, heteroaryloxy, and $-NR^eR^f$; $R_4$ is $(C_3-C_7)$alkyl or $(C_3-C_7)$alkenyl, which $(C_3-C_7)$alkyl or $(C_3-C_7)$alkenyl is optionally substituted with one or more groups independently selected from oxo, halo, hydroxy, carboxy, cyano, nitro, trifluoromethyl, trifluoromethoxy, $(C_1-C_6)$alkyl, $(C_1-C_6)$alkoxy, $(C_1-C_6)$alkoxycarbonyl, $(C_1-C_6)$alkanoyloxy, aryl, heteroaryl, aryloxy, heteroaryloxy, and $-NR^gR^h$; and $R_5$ is H, $(C_3-C_7)$alkyl or $(C_3-C_7)$alkenyl, which $(C_3-C_7)$alkyl or $(C_3-C_7)$alkenyl is optionally substituted with one or more groups independently selected from oxo, halo, hydroxy, carboxy, cyano, nitro, trifluoromethyl, trifluoromethoxy, $(C_1-C_6)$alkyl, $(C_1-C_6)$alkoxy, $(C_1-C_6)$alkoxycarbonyl, $(C_1-C_6)$alkanoyloxy, aryl, heteroaryl, aryloxy, heteroaryloxy, and $-NR^jR^k$.

In one embodiment the invention provides a compound of formula I wherein: $R_3$ is $(C_3-C_6)$alkyl or $(C_3-C_6)$alkenyl, which $(C_3-C_6)$alkyl or $(C_3-C_6)$alkenyl is optionally substituted with one or more groups independently selected from oxo, halo, hydroxy, carboxy, cyano, nitro, trifluoromethyl, trifluoromethoxy, $(C_1-C_6)$alkyl, $(C_1-C_6)$alkoxy, $(C_1-C_6)$alkoxycarbonyl, $(C_1-C_6)$alkanoyloxy, aryl, heteroaryl, aryloxy, heteroaryloxy, and $-NR^eR^f$; $R_4$ is $(C_3-C_6)$alkyl or $(C_3-C_6)$alkenyl, which $(C_3-C_6)$alkyl or $(C_3-C_6)$alkenyl is optionally substituted with one or more groups independently selected from oxo, halo, hydroxy, carboxy, cyano, nitro, trifluoromethyl, trifluoromethoxy, $(C_1-C_6)$alkyl, $(C_1-C_6)$alkoxy, $(C_1-C_6)$alkoxycarbonyl, $(C_1-C_6)$alkanoyloxy, aryl, heteroaryl, aryloxy, heteroaryloxy, and $-NR^gR^h$; and $R_5$ is H, $(C_3-C_6)$alkyl or $(C_3-C_6)$alkenyl, which $(C_3-C_6)$alkyl or $(C_3-C_6)$alkenyl is optionally substituted with one or more groups independently selected from oxo, halo, hydroxy, carboxy, cyano, nitro, trifluoromethyl, trifluoromethoxy, $(C_1-C_6)$alkyl, $(C_1-C_6)$alkoxy, $(C_1-C_6)$alkoxycarbonyl, $(C_1-C_6)$alkanoyloxy, aryl, heteroaryl, aryloxy, heteroaryloxy, and $-NR^jR^k$.

In one embodiment the invention provides a compound of formula I wherein when $R^1$ is phenyl, then at least one of $R^3$, $R^4$, and $R^5$ is other than methyl or $CH_2CH=C(CH_3)_2$.

In one embodiment the invention provides a compound of formula I wherein when $R^1$ is phenyl substituted with at least one of hydroxy, methoxy, or carboxy, then $R^4$ is other than H.

In one embodiment the invention provides a compound of formula I wherein when $R^1$ is phenyl, then at least one of $R^3$ and $R^4$ is other than methyl or $CH_2CH=C(CH_3)_2$.

In one embodiment the invention provides a compound of formula I wherein when $R^1$ is phenyl, 4-hydroxyphenyl, or 4,6-dihydroxyphenyl, then at least one of $R^4$ and $R^5$ is other than H.

Processes for preparing compounds of formula I are provided as further embodiments of the invention and are illustrated in the following schemes in which the meanings of the generic radicals are as given above unless otherwise qualified. For example, compounds of formula I can be prepared as illustrated in the following Schemes 2-6.

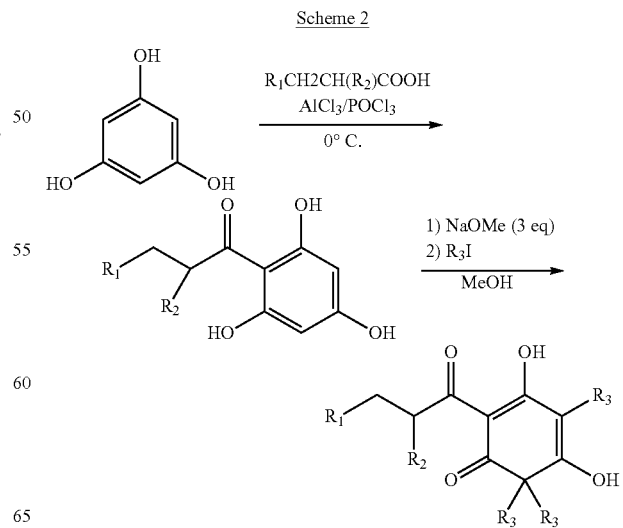

Scheme 2

Scheme 3
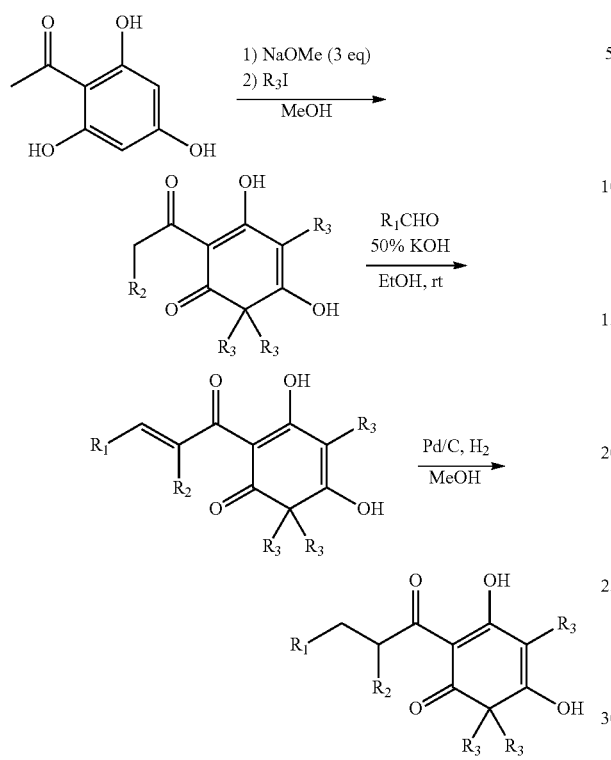
Scheme 4
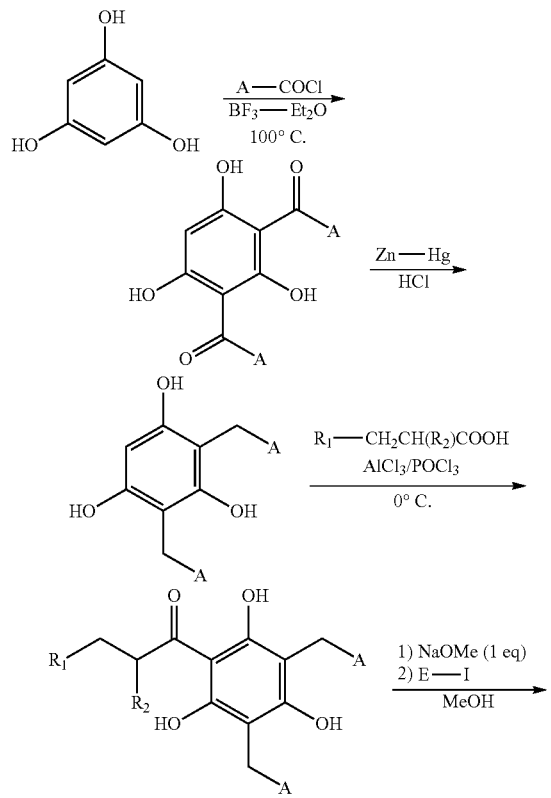
Scheme 5
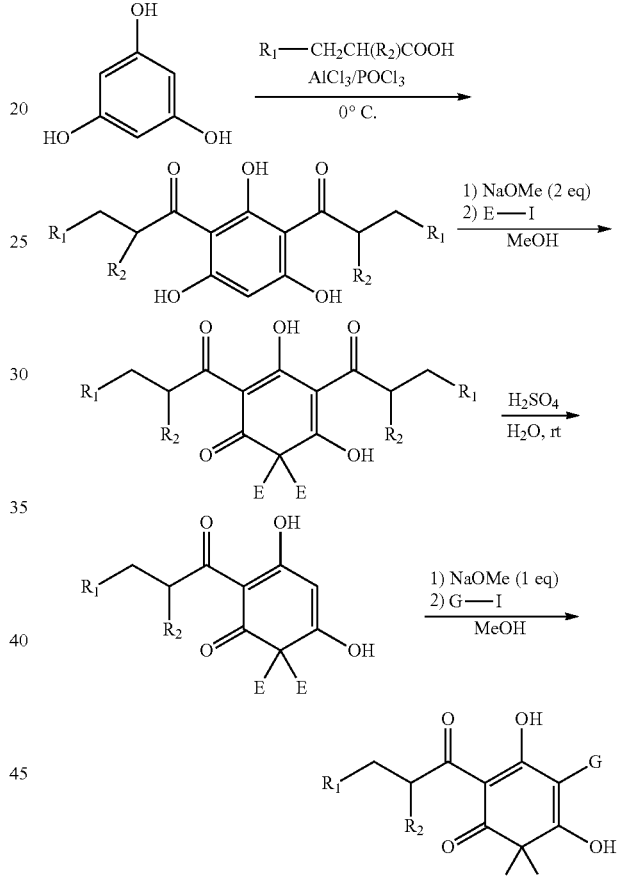
Scheme 6
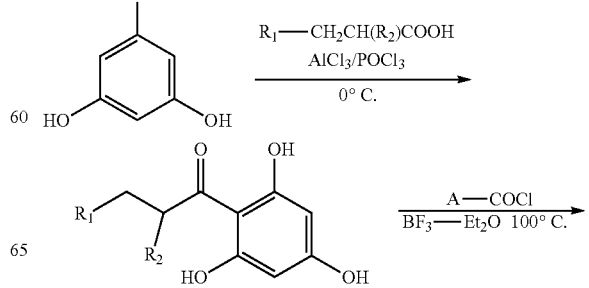

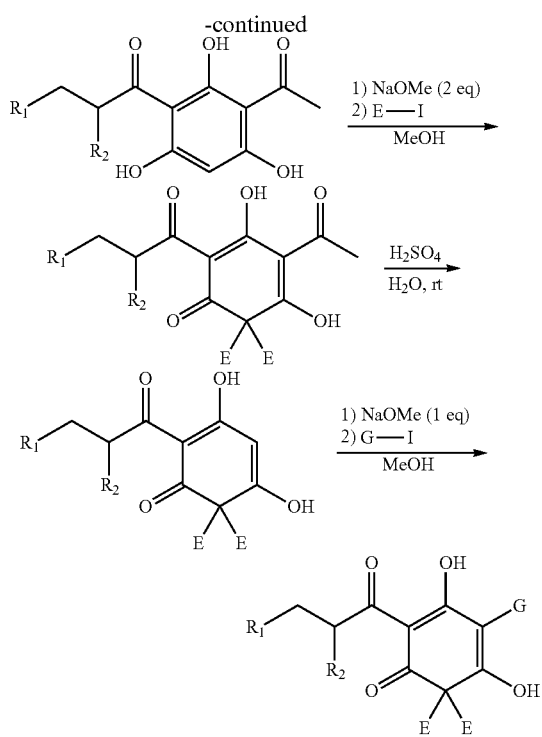

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 150 mg/kg, e.g., from about 10 to about 100 mg/kg of body weight per day, such as 3 to about 75 mg per kilogram body weight of the recipient per day, preferably in the range of 6 to 120 mg/kg/day, most preferably in the range of 15 to 90 mg/kg/day.

The compound is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of the invention formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The ability of a compound of the invention to inhibit a bacterial RNA polymerase or to inhibit a bacterial growth in culture can be determined using biochemical models that are well known to the art, or as described in the Examples.

The ability of a compound of the invention to inhibit a bacterial RNA polymerase or to inhibit bacterial growth in culture can be determined using microbiological models that are well known to the art, or as described in the Examples.

The invention will now be illustrated by the following non-limiting Examples.

EXAMPLES

Example 1. Synthesis of 3,5-dihydroxy-2-(3-(2-chlorophenyl)propanoyl)-4,6,6-triisopentylcyclohexa-2,4-dienone (1)

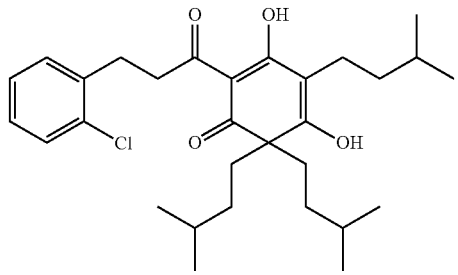

3-(2-Chlorophenyl)propanoyl-phloroglucinol (292.1 mg; 1 mmol) in 1.25 ml sodium methoxide in methanol [prepared freshly by dissolving sodium (69 mg; 3 mmol; Aldrich) in 1 ml methanol and stirring under $N_2$ for 0.5 h at 0° C.], and 1-iodo-3-methyl-butane (395 µl; 3 mmol, Aldrich) were added sequentially under $N_2$ at 0° C. to a 25 ml flame-dried two-necked round-bottom flask. The reaction mixture was stirred under $N_2$ for 4 h at 0° C. and 12 h at room temperature. The reaction mixture then was evaporated under vacuum, re-suspended in 20 ml ice water, acidified to pH≤1 by addition of 1 N HCl, and extracted with ethyl acetate (3×20 ml). The organic layer was dried over anhydrous $Na_2SO_4$ and evaporated under vacuum to yield an oily residue. The product was isolated by chromatography on silica gel. Yield: 21%. MS (MALDI): calculated, m/z 503.3 ($MH^+$). found, 503.4.

The intermediate, 3-(2-chlorophenyl)propanoyl-phloroglucinol, was prepared as follows.

a. Phloroglucinol (1.26 g, 10 mmol, Aldrich), 3-(2-chlorophenyl)propionic acid (1.84 g; 10 mmol; Alfa Aesar), and anhydrous $AlCl_3$ (5.00 g; 37.5 mmol; Aldrich) were added to a flame-dried 100 ml round-bottom flask. $POCl_3$ (25.15 g; 15 ml; 164 mmol, Aldrich) was added at 0° C. The reaction mixture was stirred under $N_2$ for 2 h at 0° C. and 8 h at room temperature and then was poured into crushed ice (100 g) and extracted with ethyl acetate (3×100 ml). The organic layer was dried over anhydrous $Na_2SO_4$ and evaporated under vacuum to yield an oily residue. 3-(2-chlorophenyl) propanoyl-phloroglucinol was isolated by chromatography on silica gel. Yield: 40%. MS (MALDI): calculated, m/z 293.1 ($MH^+$). found, 293.1.

Example 2. Synthesis of 3,5-dihydroxy-2-(3-(3-chlorophenyl)propanoyl)-4,6,6-triisopentylcyclohexa-2,4-dienone (2)

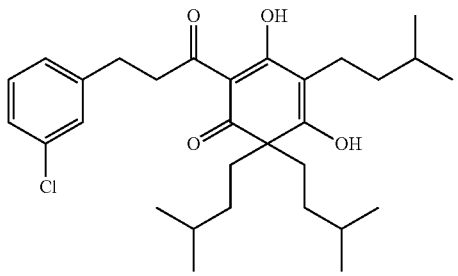

3,5-Dihydroxy-2-(3-(3-chlorophenyl)propanoyl)-4,6,6-triisopentylcyclohexa-2,4-dienone was synthesized as described in Example 1, using 3-(3-chlorophenyl)propionic acid (1.84 g; 10 mmol; Aldrich) in place of 3-(2-chlorophenyl)propionic acid and 3-(3-chlorophenyl)propanoyl-phloroglucinol (292.1 mg; 1 mmol) in place of 3-(2-chlorophenyl)propanoyl-phloroglucinol. Overall yield: 8%. MS (MALDI): calculated, m/z 503.3 (MH$^+$). found, 503.4.

Example 3. Synthesis of 3,5-dihydroxy-2-(3-(4-chlorophenyl)propanoyl)-4,6,6-triisopentylcyclohexa-2,4-dienone (3)

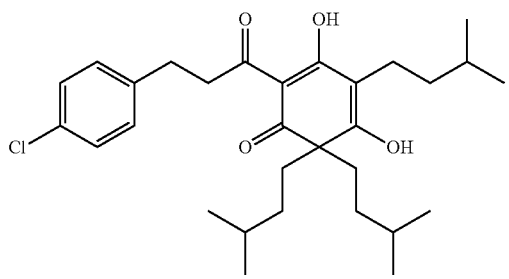

3,5-Dihydroxy-2-(3-(4-chlorophenyl)propanoyl)-4,6,6-triisopentylcyclohexa-2,4-dienone was synthesized as described in Example 1, using 3-(4-chlorophenyl)propionic acid (1.84 g; 10 mmol; Aldrich) in place of 3-(2-chlorophenyl)propionic acid and 3-(4-chlorophenyl)propanoyl-phloroglucinol (292.1 mg; 1 mmol) in place of 3-(2-chlorophenyl)propanoyl-phloroglucinol. Overall yield: 8%. MS (MALDI): calculated, m/z 503.3 (MH$^+$). found, 503.4.

Example 4. Synthesis of 3,5-dihydroxy-2-(3-(2-methoxyphenyl)propanoyl)-4,6,6-triisopentylcyclohexa-2,4-dienone (4)

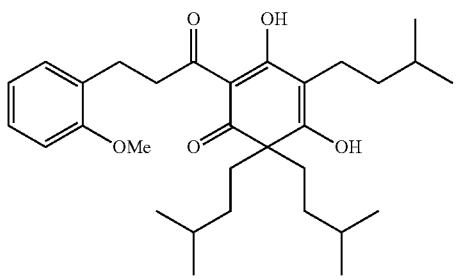

3,5-Dihydroxy-2-(3-(2-methoxyphenyl)propanoyl)-4,6,6-triisopentylcyclohexa-2,4-dienone was synthesized as described in Example 1, using 3-(2-methoxyphenyl)propionic acid (1.80 g; 10 mmol; Aldrich) in place of 3-(2-chlorophenyl)propionic acid and 3-(2-methoxyphenyl)propanoyl-phloroglucinol (288.1 mg; 1 mmol) in place of 3-(2-chlorophenyl)propanoyl-phloroglucinol. Overall yield: 8%. MS (MALDI): calculated, m/z 499.3 (MH$^+$). found, 499.5.

Example 5. Synthesis of 3,5-dihydroxy-2-(3-(3-methoxyphenyl)propanoyl)-4,6,6-triisopentylcyclohexa-2,4-dienone (5)

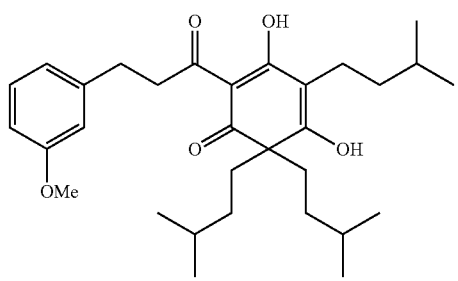 [SMILES: COc1cccc(CCC(=O)C2=C(O)C(CCC(C)C)=C(O)C(CCC(C)C)(CCC(C)C)C2=O)c1]

3,5-Dihydroxy-2-(3-(3-methoxyphenyl)propanoyl)-4,6,6-triisopentylcyclohexa-2,4-dienone was synthesized as described in Example 1, using 3-(3-methoxyphenyl)propionic acid (1.80 g; 10 mmol; Aldrich) in place of 3-(2-chlorophenyl)propionic acid and 3-(3-methoxyphenyl)propanoyl-phloroglucinol (288.1 mg; 1 mmol) in place of 3-(2-chlorophenyl)propanoyl-phloroglucinol. Overall yield: 8%. MS (MALDI): calculated, m/z 499.3 (MH$^+$). found, 499.5.

Example 6. 3,5-dihydroxy-2-(3-(4-methoxyphenyl)propanoyl)-4,6,6-triisopentylcyclohexa-2,4-dienone (6)

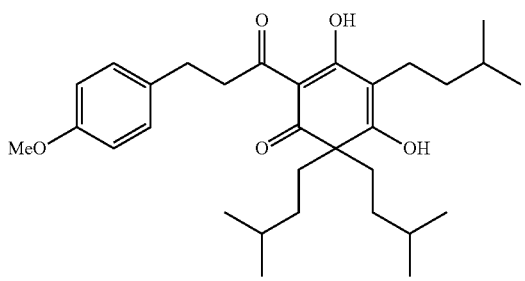 [SMILES: COc1ccc(CCC(=O)C2=C(O)C(CCC(C)C)=C(O)C(CCC(C)C)(CCC(C)C)C2=O)cc1]

3,5-Dihydroxy-2-(3-(4-methoxyphenyl)propanoyl)-4,6,6-triisopentylcyclohexa-2,4-dienone was synthesized as described in Example 1, using 3-(4-methoxyphenyl)propionic acid (1.80 g; 10 mmol; Aldrich) in place of 3-(2-chlorophenyl)propionic acid and 3-(4-methoxyphenyl)propanoyl-phloroglucinol (288.1 mg; 1 mmol) in place of 3-(2-chlorophenyl)propanoyl-phloroglucinol. Overall yield: 8%. MS (MALDI): calculated, m/z 499.3 (MH$^+$). found, 499.4.

Example 7. 3,5-dihydroxy-2-(3-(2-methylphenyl)
propanoyl)-4,6,6-triisopentylcyclohexa-2,4-dienone
(7)

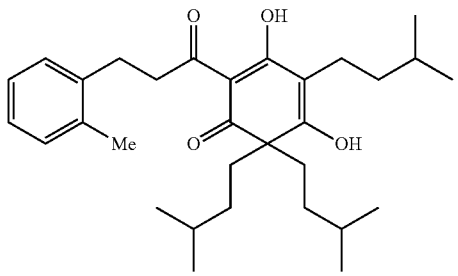 [SMILES: Cc1ccccc1CCC(=O)C1=C(O)C(CCC(C)C)=C(O)C(CCC(C)C)(CCC(C)C)C1=O]

3,5-Dihydroxy-2-(3-(2-methylphenyl)propanoyl)-4,6,6-triisopentylcyclohexa-2,4-dienone was synthesized as described in Example 1, using 3-(2-methylphenyl)propionic acid (1.64 g; 10 mmol; Aldrich) in place of 3-(2-chlorophenyl)propionic acid and 3-(2-methylphenyl)propanoyl-phloroglucinol (272.1 mg; 1 mmol) in place of 3-(2-chlorophenyl)propanoyl-phloroglucinol. Overall yield: 8%. MS (MALDI): calculated, m/z 483.4 (MH$^+$). found, 483.4.

Example 8. 3,5-dihydroxy-2-(3-(3-methylphenyl)
propanoyl)-4,6,6-triisopentylcyclohexa-2,4-dienone
(8)

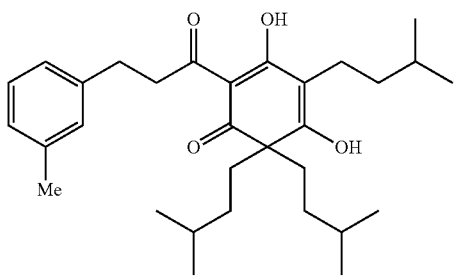 [SMILES: Cc1cccc(CCC(=O)C2=C(O)C(CCC(C)C)=C(O)C(CCC(C)C)(CCC(C)C)C2=O)c1]

3,5-Dihydroxy-2-(3-(3-methylphenyl)propanoyl)-4,6,6-triisopentylcyclohexa-2,4-dienone was synthesized as described in Example 1, using 3-(3-methylphenyl)propionic acid (1.64 g; 10 mmol; VWR) in place of 3-(2-chlorophenyl) propionic acid and 3-(3-methylphenyl)propanoyl-phloroglucinol (272.1 mg; 1 mmol) in place of 3-(2-chlorophenyl) propanoyl-phloroglucinol. Overall yield: 8%. MS (MALDI): calculated, m/z 483.4 (MH$^+$). found, 483.4.

Example 9. 3,5-dihydroxy-2-(3-(4-methylphenyl)
propanoyl)-4,6,6-triisopentylcyclohexa-2,4-dienone
(9)

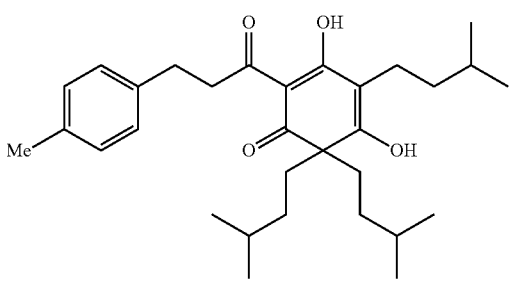 [SMILES: Cc1ccc(CCC(=O)C2=C(O)C(CCC(C)C)=C(O)C(CCC(C)C)(CCC(C)C)C2=O)cc1]

3,5-Dihydroxy-2-(3-(4-methylphenyl)propanoyl)-4,6,6-triisopentylcyclohexa-2,4-dienone was synthesized as described for in Example 1, using 3-(4-methyphenyl)propionic acid (1.64 g; 10 mmol; Aldrich) in place of 3-(2-chlorophenyl)propionic acid and 3-(4-methylphenyl)propanoyl-phloroglucinol (272.1 mg; 1 mmol) in place of 3-(2-chlorophenyl)propanoyl-phloroglucinol. Overall yield: 8%. MS (MALDI): calculated, m/z 483.4 (MH$^+$). found, 483.5.

Example 10. 3,5-dihydroxy-2-(3-(4-fluorophenyl)
propanoyl)-4,6,6-triisopentylcyclohexa-2,4-dienone
(10)

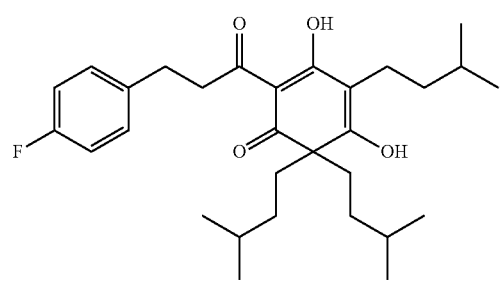 [SMILES: CC(C)CCC1=C(O)C(CCC(C)C)(CCC(C)C)C(=O)C(C(=O)CCc2ccc(F)cc2)=C1O]

3,5-Dihydroxy-2-(3-(4-fluorophenyl)propanoyl)-4,6,6-triisopentylcyclohexa-2,4-dienone was synthesized as described in Example 1, using 3-(4-fluorophenyl)propionic acid (1.68 g; 10 mmol; Aldrich) in place of 3-(2-chlorophenyl)propionic acid and 3-(4-fluorophenyl)propanoyl-phloroglucinol (276.1 mg; 1 mmol) in place of 3-(2-chlorophenyl) propanoyl-phloroglucinol. Overall yield: 8%. MS (MALDI): calculated, m/z 487.3 (MH$^+$). found, 487.4.

Example 11. 3,5-dihydroxy-2-(3-(4-bromophenyl)
propanoyl)-4,6,6-triisopentylcyclohexa-2,4-dienone
(11)

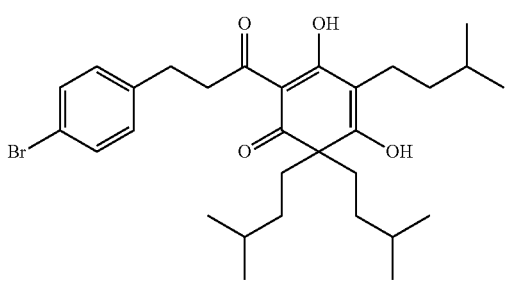 [SMILES: CC(C)CCC1=C(O)C(CCC(C)C)(CCC(C)C)C(=O)C(C(=O)CCc2ccc(Br)cc2)=C1O]

3,5-Dihydroxy-2-(3-(4-bromophenyl)propanoyl)-4,6,6-triisopentylcyclohexa-2,4-dienone was synthesized as described in Example 1, using 3-(4-bromophenyl)propionic acid (2.29 g; 10 mmol; Aldrich) in place of 3-(2-chlorophenyl)propionic acid and 3-(4-bromophenyl)propanoyl-phloroglucinol (336.0 mg; 1 mmol) in place of 3-(2-chlorophenyl)propanoyl-phloroglucinol. Overall yield: 8%. MS (MALDI): calculated, m/z 547.2 (MH$^+$). found, 547.3.

Example 12. 3,5-dihydroxy-2-(3-(4-trifluoromethylphenyl)propanoyl)-4,6,6-triisopentylcyclohexa-2,4-dienone (12)

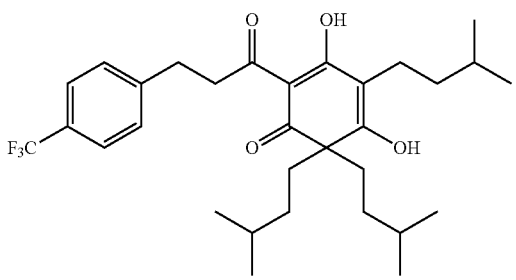

3,5-Dihydroxy-2-(3-(4-trifluoromethylphenyl)propanoyl)-4,6,6-triisopentylcyclohexa-2,4-dienone was synthesized as described in Example 1, using 3-(4-trifluoromethylphenyl)propionic acid (2.18 g; 10 mmol; Aldrich) in place of 3-(2-chlorophenyl)propionic acid and 3-(4-trifluoromethylphenyl)propanoyl-phloroglucinol (326.1 mg; 1 mmol) in place of 3-(2-chlorophenyl)propanoyl-phloroglucinol. Overall yield: 8%. MS (MALDI): calculated, m/z 537.3 (MH$^+$). found, 537.4.

Example 13. Synthesis of 3,5-dihydroxy-2-(3-(4-chlorophenyl)propanoyl)-4,6,6-tripropylcyclohexa-2,4-dienone (13)

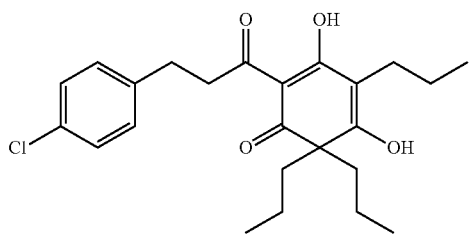 [SMILES: CCCC1=C(O)C(CCC)(CCC)C(=O)C(C(=O)CCc2ccc(Cl)cc2)=C1O]

3,5-Dihydroxy-2-(3-(4-chlorophenyl)propanoyl)-4,6,6-tripropylcyclohexa-2,4-dienone was synthesized as described in Example 1, using 3-(4-chlorophenyl)propionic acid (1.84 g; 10 mmol; Aldrich) in place of 3-(2-chlorophenyl)propionic acid, 3-(4-chlorophenyl)propanoyl-phloroglucinol (292.1 mg; 1 mmol) in place of 3-(2-chlorophenyl) propanoyl-phloroglucinol, and 1-iodopropane (293 µl; 3 mmol; Aldrich) in place of 1-iodo-3-methyl-butane. Overall yield: 8%. MS (MALDI): calculated, m/z 419.2 (MH$^+$). found, 419.2.

Example 14. Synthesis of 3,5-dihydroxy-2-(3-(4-chlorophenyl)propanoyl)-4,6,6-tributylcyclohexa-2,4-dienone (14)

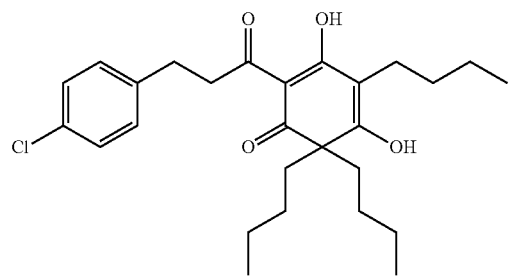 [SMILES: CCCCC1=C(O)C(CCCC)(CCCC)C(=O)C(C(=O)CCc2ccc(Cl)cc2)=C1O]

3,5-Dihydroxy-2-(3-(4-chlorophenyl)propanoyl)-4,6,6-tributylcyclohexa-2,4-dienone was synthesized as described in Example 1, using 3-(4-chlorophenyl)propionic acid (1.84 g; 10 mmol; Aldrich) in place of 3-(2-chlorophenyl)propionic acid, 3-(4-chlorophenyl)propanoyl-phloroglucinol (292.1 mg; 1 mmol) in place of 3-(2-chlorophenyl)propanoyl-phloroglucinol, and 1-iodobutane (342 µl; 3 mmol; Aldrich) in place of 1-iodo-3-methyl-butane. Overall yield: 8%. MS (MALDI): calculated, m/z 461.3 (MH$^+$). found, 461.3.

Example 15. Synthesis of 3,5-dihydroxy-2-(3-phenylpropanoyl)-4,6,6-triisopentylcyclohexa-2,4-dienone (15)

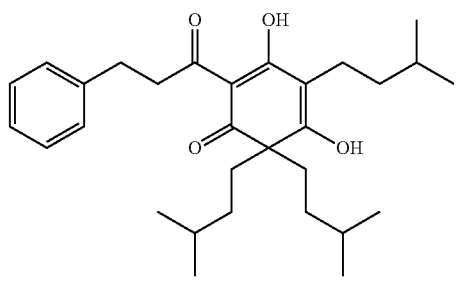 [SMILES: CC(C)CCC1=C(O)C(CCC(C)C)(CCC(C)C)C(=O)C(C(=O)CCc2ccccc2)=C1O]

3-Phenylpropanoyl-phloroglucinol (258.27 mg; 1 mmol) in 1.25 ml sodium methoxide in methanol [prepared freshly by dissolving sodium (69 mg; 3 mmol; Aldrich) in 1 ml methanol and stirring under N$_2$ for 0.5 h at 0° C.], and 1-iodo-3-methyl-butane (395 µl; 3 mmol, Aldrich) were added sequentially under N$_2$ at 0° C. to a 25 ml flame-dried two-necked round-bottom flask. The reaction mixture was stirred under N$_2$ for 4 h at 0° C. and 12 h at room temperature. The reaction mixcture then was evaporated under vacuum, re-suspended in 20 ml ice water, acidified to pH≤1 by addition of 1 N HCl, and extracted with ethyl acetate (3×20 ml). The organic layer was dried over anhydrous Na$_2$SO$_4$ and evaporated under vacuum to yield an oily residue. Product 2 was isolated by chromatography on silica gel. Yield: 17%. MS (MALDI): calculated, m/z 469.3 (MH$^+$). found, 469.2.

The intermediate, 3-phenylpropanoyl-phloroglucinol, was prepared as follows.

a. Phloroglucinol (1.26 g, 10 mmol, Aldrich), 3-phenylpropionic acid (1.50 g; 10 mmol; Aldrich), and anhydrous AlCl$_3$ (5.00 g; 37.5 mmol; Aldrich) were added to a flame-dried 100 ml round-bottom flask. POCl$_3$ (25.15 g; 15 ml; 164 mmol, Aldrich) was added at 0° C. The reaction mixture was stirred under N$_2$ for 2 h at 0° C. and 8 h at room temperature and then was poured into crushed ice (100 g) and extracted with ethyl acetate (3×100 ml). The organic layer was dried over anhydrous Na$_2$SO$_4$ and evaporated under vacuum to yield an oily residue. 3-phenylpropanoyl-phloroglucinol was isolated by chromatography on silica gel. Yield: 20-30%. MS (MALDI): calculated, m/z 259.1 (MH$^+$). found, 259.0.

Example 16. Synthesis of 3,5-dihydroxy-2-(3-phenylpropanoyl)-4,6,6-triethylcyclohexa-2,4-dienone (16)

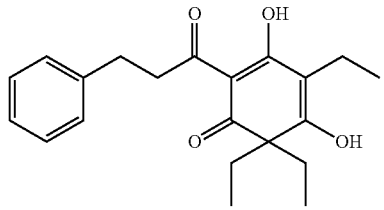 [SMILES: CCC1=C(O)C(CC)(CC)C(=O)C(C(=O)CCc2ccccc2)=C1O]

3,5-dihydroxy-2-(3-phenylpropanoyl)-4,6,6-triethylcyclohexa-2,4-dienone was synthesized as described in Example 15, using 1-iodoethane (241 µl; 3 mmol; Aldrich) in place of 1-iodo-3-methyl-butane. Yield: 20%. MS (MALDI): calculated, m/z 343.2 (MH$^+$). found, 343.2.

Example 17. Synthesis of 3,5-dihydroxy-2-(3-phenylpropanoyl)-4,6,6-tripropylcyclohexa-2,4-dienone (17)

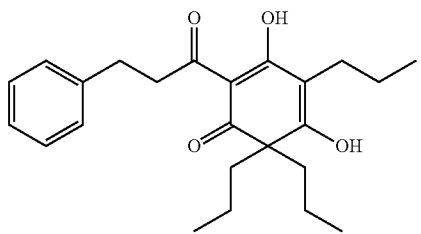 [SMILES: CCCC1=C(O)C(CCC)(CCC)C(=O)C(C(=O)CCc2ccccc2)=C1O]

3,5-Dihydroxy-2-(3-phenylpropanoyl)-4,6,6-tripropylcyclohexa-2,4-dienone was synthesized as described in Example 15, using 1-iodopropane (293 µl; 3 mmol; Aldrich) in place of 1-iodo-3-methyl-butane. Overall yield: 5%. MS (MALDI): calculated, m/z 385.2 (MH$^+$). found, 385.2.

Example 18. Synthesis of 3,5-dihydroxy-2-(3-phenylpropanoyl)-4,6,6-tributylcyclohexa-2,4-dienone (18)

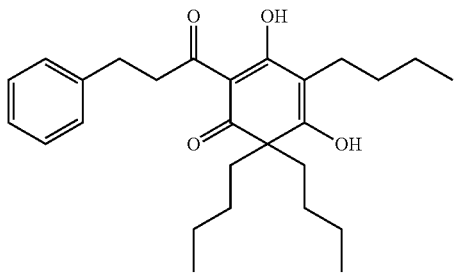 [SMILES: CCCCC1=C(O)C(CCCC)(CCCC)C(=O)C(C(=O)CCc2ccccc2)=C1O]

3,5-Dihydroxy-2-(3-phenylpropanoyl)-4,6,6-tributylcyclohexa-2,4-dienone was synthesized as described in Example 15, using 1-iodobutane (342 µl; 3 mmol; Aldrich) in place of 1-iodo-3-methyl-butane. Overall yield: 64%. MS (MALDI): calculated, m/z 427.3 (MH$^+$). found, 427.3.

Example 19. Synthesis of 3,5-dihydroxy-2-(3-phenylpropanoyl)-4,6,6-tripentylcyclohexa-2,4-dienone (19)

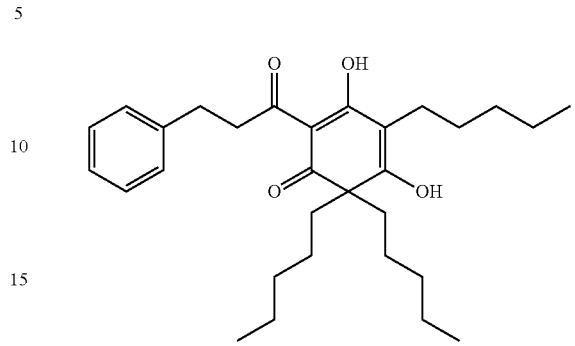

3,5-Dihydroxy-2-(3-phenylpropanoyl)-4,6,6-tripentylcyclohexa-2,4-dienone was synthesized as described in Example 15, using 1-iodopentane (393 µl; 3 mmol; Aldrich) in place of 1-iodo-3-methyl-butane. Overall yield: 5%. MS (MALDI): calculated, m/z 469.3 (MH$^+$). found, 469.3.

Example 20. Synthesis of 3,5-dihydroxy-2-(2-methyl-3-phenylpropanoyl)-4,6,6-triisopentylcyclohexa-2,4-dienone (20)

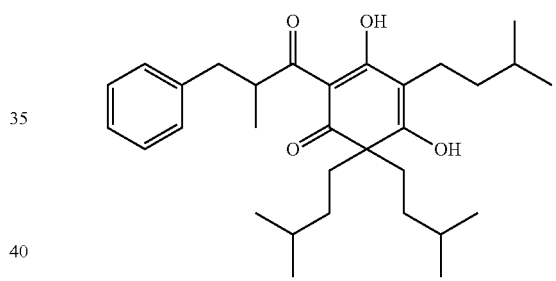

3,5-Dihydroxy-2-(2-methyl-3-phenylpropanoyl)-4,6,6-triisopentylcyclohexa-2,4-dienone was synthesized as described in Example 15, using 2-methyl-3-phenylpropanoyl-phloroglucinol (270.3 mg; 1 mmol; Aldrich) in place of 3-phenylpropanoyl-phloroglucinol. Yield: 13%. MS (MALDI): calculated, m/z 483.3 (MH$^+$). found, 483.3.

The intermediate 2-methyl-3-phenylpropanoyl-phloroglucinol was prepared as follows.

a. 2-Methyl-3-phenylpropanoyl-phloroglucinol was synthesized as described for 3-phenylpropanoyl-phloroglucinol in Example 15, using 2-methyl-3-phenylpropionic acid (1.64 g; 10 mmol; Aldrich) in place of 3-phenylpropionic acid. Yield: 13%. MS (MALDI): calculated: m/z 273.1 (MH$^+$). found, 273.1.

Example 21. Assay of Inhibition of Bacterial RNA Polymerase

Example 21.1. Assay of Inhibition of *Escherichia coli* RNA Polymerase

Fluorescence-detected RNA polymerase assays with *E. coli* RNA polymerase were performed by a modification of the procedure of Kuhlman et al., 2004 [Kuhlman, P., Duff, H. & Galant, A. (2004) A fluorescence-based assay for multisubunit DNA-dependent RNA polymerases. *Anal. Biochem.* 324, 183-190]. Reaction mixtures contained (20 µl): 0-100 nM test compound, 75 nM *E. coli* RNA polymerase $\sigma^{70}$ holoenzyme, 20 nM 384 bp DNA fragment containing the bacteriophage T4 N25 promoter, 100 µM ATP, 100 µM GTP, 100 µM UTP, 100 µM CTP, 50 mM Tris-HCl, pH 8.0, 100 mM KCl, 10 mM $MgCl_2$, 1 mM DTT, 10 µg/ml bovine serum albumin, and 5.5% glycerol. Reaction components other than DNA and NTPs were pre-incubated for 10 min at 37° C. Reactions were carried out by addition of DNA and incubation for 5 min at 37° C., followed by addition of NTPs and incubation for 60 min at 37° C. DNA was removed by addition of 1 µl 5 mM $CaCl_2$ and 2 U DNaseI (Ambion, Inc.), followed by incubation for 90 min at 37° C. RNA was quantified by addition of 100 µl RiboGreen RNA Quantitation Reagent (Invitrogen, Inc.; 1:500 dilution in Tris-HCl, pH 8.0, 1 mM EDTA), followed by incubation for 10 min at 25° C., followed by measurement of fluorescence intensity [excitation wavelength=485 nm and emission wavelength=535 nm; QuantaMaster QM1 spectrofluorometer (PTI, Inc.)]. IC50 is defined as the concentration of inhibitor resulting in 50% inhibition of RNA polymerase activity.

Example 21.2. Assay of Inhibition of *Mycobacterium tuberculosis* RNA Polymerase Fluorescence-detected RNA polymerase assays with *M. tuberculosis* RNA polymerase were performed as in Example 21.1, using reaction mixtures containing (20 µl): 0-100 nM test compound, 75 nM *M. tuberculosis* RNA polymerase core enzyme, 300 nM *M. tuberculosis* $\sigma^{A}$, 20 nM 384 bp DNA fragment containing the bacteriophage T4 N25 promoter, 100 µM ATP, 100 µM GTP, 100 µM UTP, 100 µM CTP, 40 mM Tris-HCl, pH 8.0, 80 mM NaCl, 5 mM $MgCl_2$, 2.5 mM DTT, and 12.7% glycerol. IC50 is defined as the concentration of inhibitor resulting in 50% inhibition of RNA polymerase activity.

Example 21.3. Assay of Inhibition of *Staphylococcus Aureus* RNA Polymerase

Fluorescence-detected RNA polymerase assays with *S. aureus* RNA polymerase were performed as in Example 21.1, using reaction mixtures containing (20 µl): 0-100 nM test compound, 75 nM *S. aureus* RNA polymerase core enzyme, 300 nM *S. aureus* $\sigma^{A}$, 20 nM 384 bp DNA fragment containing the bacteriophage T4 N25 promoter, 100 µM ATP, 100 µM GTP, 100 µM UTP, 100 µM CTP, 40 mM Tris-HCl, pH 8.0, 80 mM NaCl, 5 mM $MgCl_2$, 2.5 mM DTT, and 12.7% glycerol. IC50 is defined as the concentration of inhibitor resulting in 50% inhibition of RNA polymerase activity.

Example 22. Assay of Inhibition of Bacterial Growth in Culture

Example 22.1. Assay of Inhibition of Growth of *Staphylococcus Aureus*, *Enterococcus Faecalis*, *Enterococcus Faecium*, and *Escherichia Coli*

Minimum inhibitory concentrations (MICs) for *Staphylococcus aureus* ATCC 12600, *Staphylococcus aureus* ATCC 13709 MSSA, *Staphylococcus aureus* BAA-1707 MRSA (MW2), *Staphylococcus aureus* BAA-1717 MRSA (USA300), *Enterococcus faecalis* ATCC 19433, *Enterococcus faecium* ATCC 19434, and *Escherichia coli* D21f2tolC were quantified using spiral gradient endpoint assays, essentially as described [Wallace, A. and Corkill, J. (1989) Application of the spiral plating method to study antimicrobial action. *J. Microbiol. Meths.* 10, 3030-310; Paton, J., Holt, A., and Bywater, M. (1990) Measurement of MICs of antibacterial agents by spiral gradient endpoint compared with conventional dilution methods. *Int. J. Exp. Clin. Chemother.* 3, 31-38; Schalkowsky S. (1994) Measures of susceptibility from a spiral gradient of drug concentrations. *Adv. Exp. Med. Biol.* 349, 107-120]. Assays employed exponential-gradient plates containing 150 mm×4 mm Mueller-Hinton II cation-adjusted agar and 0.4-40 µg/ml of test compound. Plates were prepared using an Autoplate 4000 spiral plater (Spiral Biotech, Inc.). Saturated overnight cultures were swabbed radially onto plates, and plates were incubated for 16 h at 37° C. For each culture, the streak length was measured using a clear plastic template (Spiral Biotech, Inc.), the test-compound concentration at the streak endpoint was calculated using the program SGE (Spiral Biotech, Inc.), and the MIC was defined as the calculated test-compound concentration at the streak endpoint.

Example 22.2 Assay of Inhibition of Growth of *Streptococcus Pneumoniae* and *Streptococcus Pyogenes*, and *Moraxella Catarrhalis*

Minimum inhibitory concentrations (MICs) for *Streptococcus pneumoniae* ATCC 49619, *Streptococcus pyogenes* ATCC 12344, and *Moraxella catarrhalis* ATCC 25238 were quantified using spiral gradient endpoint assays, as in Example 22.1, except that plates contained GC II agar and were incubated in a 5% $CO_2$/95% air atmosphere.

Example 22.3. Assay of Inhibition of Growth of *Mycobacterium tuberculosis*

Minimum inhibitory concentrations (MICs) for *Mycobacterium tuberculosis* were quantified using microplate Alamar Blue assays as described [Collins, L. & Franzblau, S. (1997) Microplate Alamar Blue assay versus BACTEC 460 system for high-throughput screening of compounds against *Mycobacterium tuberculosis* and *Mycobacterium avium*. *Antimicrob. Agents Chemother.* 41, 1004-1009].

Example 22.4. Assay of Inhibition of Growth of *Bacillus Anthracis* and *Francisella* Tularensis Minimum inhibitory concentrations (MICs) for *Bacillus anthracis*, and *Francisella tularensis* were quantified using broth microdilution assays as described [Clinical and Laboratory Standards Institute (CLSI/NCCLS) (2009) *Methods for Dilution Antimicrobial Susceptibility Tests for Bacteria That Grow Aerobically; Approved Standard, Eighth Edition*. CLIS Document M07-A8 (CLIS, Wayne Pa.)].

Screening Data for representative compounds of the invention is presented in the following Tables.

| Compound | IC50 *E. coli* RNAP (μM) | IC50 *M. tuberculosis* RNAP (μM) | IC50 *S. aureus* RNAP (μM) | MIC *M. tuberculosis* H37Rv (μg/ml) | MIC *S. aureus* 12600 (μg/ml) | MIC *S. aureus* 13709 (μg/ml) | MIC *S. aureus* MRSA 1707 (μg/ml) | MIC *S. aureus* MRSA 1717 (μg/ml) |
|---|---|---|---|---|---|---|---|---|
| 15 | 3.5 | 2.6 | 11 | 50 | 0.5 | 0.5 | 0.4 | 0.5 |
| 16 | >400 | >400 | >400 | >50 | 4 | 6 | 6 | 8 |
| 17 | 70 | 140 | >400 | >50 | 1 | 2 | 2 | 2 |
| 18 | 33 | 22 | 80 | 50 | <0.5 | 0.8 | 0.8 | <0.5 |
| 19 | 7.3 | 4.1 | 13 | 50 | 2 | 3 | 0.7 | 1 |
| 20 | 12 | 7.3 | 13 | 50 | 0.4 | 0.7 | 0.7 | 0.7 |
| 1 | 2.1 | 1.2 | 5.7 | 50 | 0.6 | | | |
| 2 | 2.5 | 2.2 | 5.9 | 50 | 0.5 | | | |
| 3 | 0.63 | 0.77 | 2.4 | 50 | 0.4 | | | |
| 4 | 1.9 | 1.6 | 4.3 | >50 | 0.6 | | | |
| 5 | 1.1 | 1.1 | 3.1 | 50 | 0.4 | | | |
| 6 | 1.8 | 1.2 | 3.4 | 50 | 0.6 | | | |
| 7 | 0.21 | 0.17 | 1.1 | 50 | 0.5 | | | |
| 8 | 0.42 | 0.6 | 2.2 | >50 | 4 | | | |
| 9 | 0.22 | 0.29 | 0.84 | 25 | 0.5 | | | |
| 10 | 0.53 | 0.64 | 2.2 | 50 | 0.5 | | | |
| 11 | 0.89 | 0.78 | 3.3 | 50 | 0.8 | | | |
| 12 | 0.12 | 0.22 | 0.46 | 25 | 0.6 | | | |
| 13 | 7.8 | 1.4 | 5.3 | >50 | 0.7 | | | |
| 14 | 1.1 | 0.68 | 3.1 | >50 | 0.5 | | | |

| Compound | MIC *E. faecalis* 19433 (μg/ml) | MIC *E. faecium* 19434 (μg/ml) | MIC *S. pneumoniae* 49619 (μg/ml) | MIC *S. pyogenes* 12344 (μg/ml) |
|---|---|---|---|---|
| 15 | 1 | 1.5 | 12 | 12 |
| 16 | 19 | 5 | 15 | 19 |
| 17 | 3 | 1 | 15 | 19 |
| 18 | 11 | 0.6 | 9.3 | 12 |
| 19 | 9 | 2 | 15 | 15 |
| 20 | 0.7 | 0.6 | 19 | 15 |
| 1 | 2 | | 15 | 19 |
| 2 | 1 | | 12 | 19 |
| 3 | 1 | | 19 | 19 |
| 4 | 3 | | 2.7 | 15 |
| 5 | 2 | | 3.5 | 7.1 |
| 6 | 12 | | 5.6 | 15 |
| 7 | 1 | | | |
| 8 | 1 | | | |
| 9 | 1 | | | |
| 10 | 2.7 | | | |
| 11 | 2.6 | | | |
| 12 | 0.5 | | | |
| 13 | 2.2 | | | |
| 14 | 1.3 | | | |

| Compound | MIC *B. anthracis* Vollum-1b (μg/ml) | MIC *E. coli* D21f2tolC (μg/ml) | MIC *M. catarrhalis* 25238 (μg/ml) | MIC *F. tularensis* SCHU4 (μg/ml) |
|---|---|---|---|---|
| 15 | 0.098 | 4 | 25 | 0.19 |
| 16 | | 5 | >40 | |
| 17 | | 1.3 | >40 | |
| 18 | 0.049 | 1.2 | 24 | 25 |
| 19 | 0.049 | 14 | 19 | 0.39 |
| 20 | 0.098 | 6 | 24 | 0.78 |
| 1 | 0.049 | 24 | >40 | 6.25 |
| 2 | 0.098 | 15 | 19 | >50 |
| 3 | 0.049 | 8 | 19 | >50 |
| 4 | 0.098 | 12 | >40 | >50 |
| 5 | 0.049 | 2 | 19 | 1.56 |
| 6 | 0.098 | 6 | 19 | >50 |
| 7 | | 7 | | |
| 8 | | 12 | | |
| 9 | | 4.4 | | |
| 10 | | 2.7 | | |

-continued

| Compound | MIC *B. anthracis* Vollum-1b (μg/ml) | MIC *E. coli* D21f2tolC (μg/ml) | MIC *M. catarrhalis* 25238 (μg/ml) | MIC *F. tularensis* SCHU4 (μg/ml) |
|---|---|---|---|---|
| 11 | | 3.3 | | |
| 12 | | 4.3 | | |
| 13 | | 0.8 | | |
| 14 | | 0.6 | | |

Example 23

The following illustrate representative pharmaceutical dosage forms, containing a compound of formula I ('Compound X'), for therapeutic or prophylactic use in humans

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 1.0N Sodium hydroxide solution (pH adjustment to 7.0-7.5) | q.s. |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |

-continued

| (vi) Aerosol | mg/can |
|---|---|
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound having the following structure:

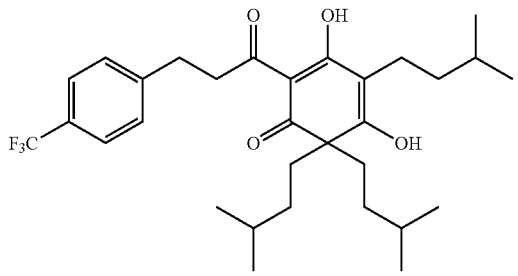 [SMILES: CC(C)CCC1=C(O)C(CCC(C)C)(CCC(C)C)C(=O)C(C(=O)CCc2ccc(C(F)(F)F)cc2)=C1O]

or a tautomer thereof, or a pharmaceutically acceptable salt thereof.

2. A composition comprising the compound of claim 1 or a tautomer thereof, or a pharmaceutically acceptable salt thereof, and a pharmaceutically acceptable vehicle.

* * * * *